US010179252B2

(12) United States Patent
Timmer et al.

(10) Patent No.: US 10,179,252 B2
(45) Date of Patent: Jan. 15, 2019

(54) IRRADIATION DEVICE AND METHOD

(71) Applicant: VARIAN MEDICAL SYSTEMS PARTICLE THERAPY GmbH, Troisdorf (DE)

(72) Inventors: Jan Timmer, San Jose, CA (US); Juergen Schultheiss, Cologne (DE); L. Alberto Cruz, Guangdong (CN); Michael Schillo, Bonn (DE)

(*) Notice: Subject to any disclaimer, the term of this patent is extended or adjusted under 35 U.S.C. 154(b) by 124 days.

(21) Appl. No.: 14/909,780

(22) PCT Filed: Dec. 15, 2014

(86) PCT No.: PCT/EP2014/003360
§ 371 (c)(1),
(2) Date: Feb. 3, 2016

(87) PCT Pub. No.: WO2015/090555
PCT Pub. Date: Jun. 25, 2015

(65) Prior Publication Data
US 2016/0279447 A1    Sep. 29, 2016

(30) Foreign Application Priority Data

Dec. 17, 2013 (EP) .................................... 13005874

(51) Int. Cl.
*A61N 5/10* (2006.01)
*H05H 7/00* (2006.01)
*H01J 37/08* (2006.01)

(52) U.S. Cl.
CPC .......... *A61N 5/1082* (2013.01); *A61N 5/107* (2013.01); *A61N 5/1081* (2013.01); *H01J 37/08* (2013.01);

(Continued)

(58) Field of Classification Search
CPC ................. A61N 2005/1087; A61N 2005/109
See application file for complete search history.

(56) References Cited

U.S. PATENT DOCUMENTS

| 4,870,287 A | 9/1989 | Cole et al. |
| 5,523,659 A | 6/1996 | Swenson |

(Continued)

FOREIGN PATENT DOCUMENTS

| CN | 102387836 A | 3/2012 |
| CN | 103153397 A | 6/2013 |

(Continued)

OTHER PUBLICATIONS

International Search Report and Written Opinion dated Jan. 8, 2016, in PCT/US2015/16239.

(Continued)

*Primary Examiner* — Thaddeus B Cox
(74) *Attorney, Agent, or Firm* — Shapiro, Gabor and Rosenberger, PLLC

(57) ABSTRACT

Irradiation device for irradiating an irradiation object with heavy charged particles, comprising a support for the irradiation object, and an irradiation nozzle irradiating a charged particle beam towards the irradiation object, wherein the beam is deflected within the irradiation nozzle. The support for the irradiation object is moveable at least horizontally, and the irradiation nozzle is moveable at least vertically and rotatable around a nozzle swivel axis along which the particle beam enters into the irradiation nozzle.

46 Claims, 19 Drawing Sheets

Figure 1:
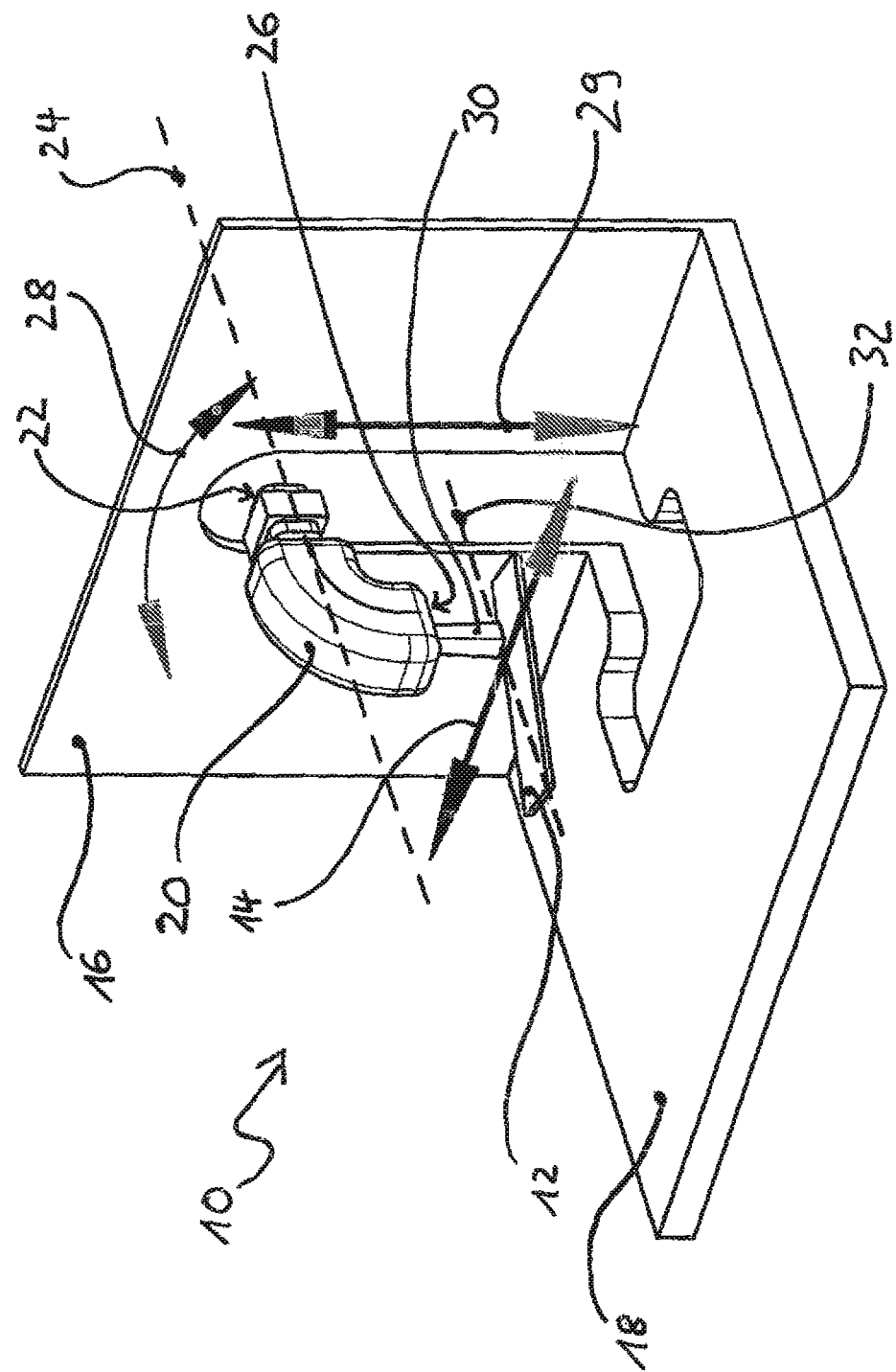

(52) U.S. Cl.
CPC ........... *H05H 7/001* (2013.01); *A61N 5/1067* (2013.01); *A61N 2005/1087* (2013.01); *H05H 2007/002* (2013.01); *H05H 2277/11* (2013.01)

(56) References Cited

U.S. PATENT DOCUMENTS

| | | | |
|---|---|---|---|
| 6,172,463 | B1 | 1/2001 | Cutler et al. |
| 7,432,516 | B2 | 10/2008 | Peggs et al. |
| 8,053,746 | B2 | 11/2011 | Timmer et al. |
| 2004/0184579 | A1* | 9/2004 | Mihara .................... A61N 5/10 378/65 |
| 2006/0193435 | A1* | 8/2006 | Hara .................... A61N 5/1049 378/65 |
| 2007/0170994 | A1 | 7/2007 | Peggs et al. |
| 2011/0017920 | A1* | 1/2011 | Goer ........................ A61N 5/10 250/396 R |
| 2011/0182410 | A1 | 7/2011 | Balakin |
| 2012/0119105 | A1 | 5/2012 | Iwata |
| 2012/0203490 | A1* | 8/2012 | Sayeh ..................... G21K 1/04 702/105 |
| 2013/0015364 | A1 | 1/2013 | Mackinnon et al. |
| 2013/0178690 | A1* | 7/2013 | Masumoto ........... A61N 5/1037 600/1 |
| 2013/0289330 | A1 | 10/2013 | Haruna et al. |
| 2014/0048718 | A1 | 2/2014 | Sano |

FOREIGN PATENT DOCUMENTS

| | | |
|---|---|---|
| CN | 103492025 A | 1/2014 |
| DE | 202006019307 U1 | 5/2008 |
| JP | 2001-178834 A | 7/2001 |
| WO | WO 9606445 A1 | 2/1996 |
| WO | WO 0028797 A1 | 5/2000 |

OTHER PUBLICATIONS

International Search Report and Written Opinion dated Feb. 19, 2015, in International Application No. PCT/EP2014/003360.
Office Action and Search Report dated Apr. 28, 2018, in Chinese Application No. 2014800491020.
Office Action dated Jun. 4, 2018, in Chinese Application No. 2015800450152.
European Search Report dated Mar. 12, 2018, in European Application No. 15833367.4.
Office Action dated Aug. 6, 2018, in Japanese Patent Application No. 2016-559512.

* cited by examiner

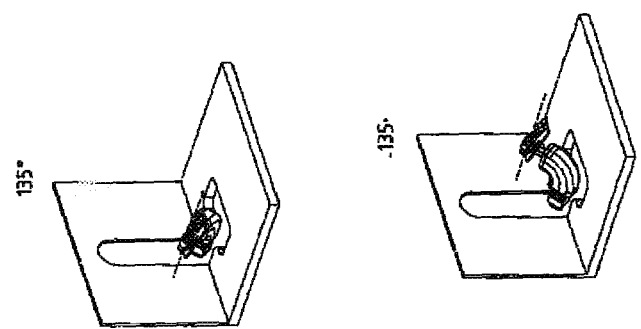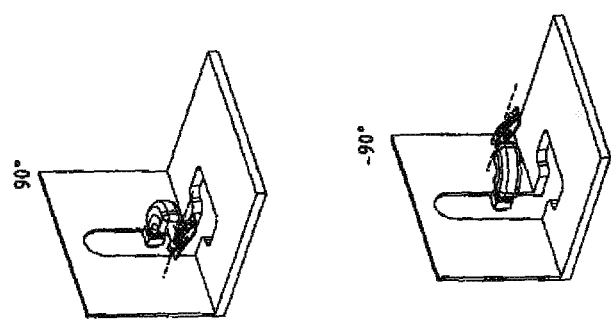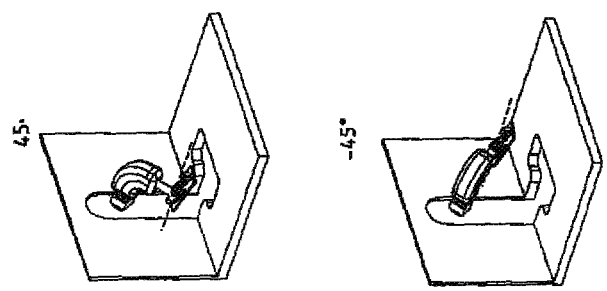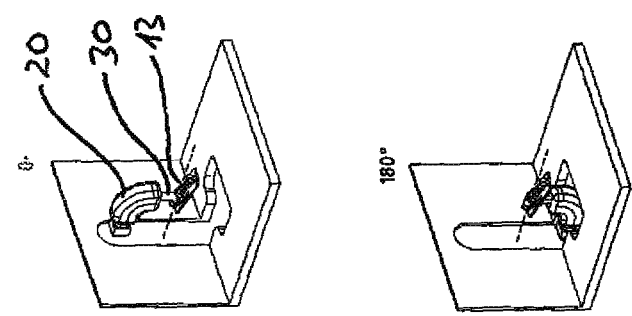
Fig. 7

IRRADIATION DEVICE AND METHOD

The invention relates to an irradiation device for irradiating an irradiation object from various angles with heavy charged particles. Heavy charged particles are understood to be charged particles which contain at least one nucleon (proton or neutron). Such devices are used for instance in particle therapy systems for irradiating and destroying tumours with protons or heavier ions.

A proton therapy system with a plurality of treatment stations is known from U.S. Pat. No. 4,870,287. Such systems comprise a proton accelerator, for example a cyclotron, for providing a proton beam, and a beam guiding system for guiding the proton beam in a vacuum environment to so called gantries, which allow the proton beam to impinge from different angular directions onto the irradiation object placed centrically at the treatment station. Such gantry is a pivotably mounted device, in which the proton beam arriving along the swivel axis is coupled in, and in which the beam is deflected away from the swivel axis and guided onwards by suitable beam optics in such way that by rotating the gantry around its swivel axis the beam impinges onto the irradiation object located in the region of the swivel axis of the gantry from different directions.

Another gantry design is known from the irradiation device described in DE 20 2006 019 307. In this design, the accelerator is mounted on a pivotable U-shaped frame, and the beam is guided along the U-shaped structure so as to impinge onto the irradiation object located in the region of the swivelling axis of the gantry frame.

The known gantry designs require quite complex and bulky structures, in particular due to the fact that the gantry has to be turned by 360° all around the irradiation object, in order to be able to irradiate the irradiation object from all angular directions. Therefore, it is an object of the present invention to propose an improved gantry design, in particular a more simple gantry design.

In accordance with the invention, this object is solved by an irradiation device with the features of claim 1 and by an irradiation method with the features of claim 14. Preferred aspects are subject of the dependent claims.

The irradiation device according to the invention comprises a support for the irradiation object and an irradiation nozzle for irradiating the charged particle beam towards the irradiation object. Preferably, the nozzle comprises means for scattering and/or scanning the beam according to known technologies in order to achieve a good dose conformation in the irradiation object. The beam, which may be generated by a beam source and guided to the irradiation nozzle by suitable beam guidance means, enters into the irradiation nozzle along a certain direction. Within the irradiation nozzle, the beam is deflected away from the entrance direction. Preferably, the beam—or, in case of scattering and/or scanning, the beam and/or scan centre—is deflected by 90° such that the beam leaves the irradiation nozzle in a direction perpendicular to the entrance direction. The deflection can preferably be achieved by suitable deflection magnets or other deflection devices. According to the invention, the support for the irradiation object can be moved at least horizontally. This movement is understood to be a movement which has at least a horizontal translational component. The irradiation nozzle can be moved at least vertically, and this movement is understood to be a movement which has at least a vertical translational component. In addition, the irradiation nozzle can be rotated around a nozzle swivel axis, and the particle beam enters into the irradiation nozzle along the nozzle swivel axis. This set-up allows to irradiate the irradiation object from various angular directions, whereby the change of the angular direction can be achieved by a vertical movement of the nozzle, because the beam can be kept impinging onto the irradiation object by suitably rotating the irradiation nozzle around the nozzle swivel axis and/or suitably horizontally moving the support of the irradiation object. In case of particle therapy, the invention allows to avoid a vertical movement of the irradiation object, i. e. the patient, while irradiating it from all angular directions.

In a preferred aspect, the nozzle swivel axis is horizontal. This allows a more simple design of the irradiation device, in particular in combination with the preferred deflection of the beam within the irradiation nozzle by 90°. If the nozzle swivel axis is horizontal and the beam is deflected within the irradiation nozzle by 90°, the plane described by the beam when rotating the irradiation nozzle is vertical.

In another preferred aspect, the vertical and rotary movement of the nozzle is coordinated by control means. The control means control the lateral position and the angular direction of the particle beam irradiated from the irradiation nozzle.

In another preferred aspect, at least two of the three movements
(i) horizontal movement of the support
(ii) vertical movement of the nozzle
(iii) rotary movement of the nozzle
are coordinated by the control means in such way that the particle beam keeps impinging onto the irradiation object when the support and/or the nozzle are moved. This allows to irradiate the irradiation object from various angular directions.

In a more preferred aspect, the horizontal movement of the support and the vertical and rotary movement of the nozzle are coordinated in such way that the particle beam keeps impinging onto the irradiation object at a defined distance from the irradiation nozzle when the support and/or the nozzle are moved. More preferably the distance between the irradiation nozzle and the irradiation object is kept constant when the support and/or the nozzle are moved. This allows to irradiate the irradiation object from different angular directions but at same distance from the irradiation nozzle.

In case of particle therapy, the control means may preferably include known patient position verification systems for verifying the position of the irradiation object and generating on this basis control signals for controlling the movement of the support and the nozzle.

In another preferred aspect, the angle between the direction of the beam impinging onto the irradiation object and the vertical direction can be varied between 0° and 180°. More preferably, this angle can be varied between −180° and +180°. In another preferred aspect, this angle can be varied continuously. This allows to irradiate the irradiation object from all angular directions.

In another preferred aspect, the support for the irradiation object is turnable around a vertical axis, preferably by 180°. This allows to irradiate the irradiation object from all angular directions, even if the angle between the beam and the vertical direction can be varied only between 0° and +180°.

In another preferred aspect, the vertical movement of the irradiation nozzle is effected by a pivotable cantilever arm. The cantilever arm is part of the beam transport system transporting the beam from the beam source to the irradiation nozzle, which forms end portion of the cantilever arm. The beam enters the cantilever arm along the cantilever swivel axis around which the cantilever arm is pivotable. The cantilever arm comprises beam guidance means guiding the beam from the entrance into the cantilever arm to the irradiation nozzle. A first beam deflector deflects the beam entering into the cantilever arm away from the cantilever arm swivel axis, preferably by 90°. Furthermore, the cantilever arm comprises, downstream from the first deflector, a second deflector deflecting the particle beam into the irradiation nozzle. By rotating the cantilever arm around its swivel axis, the irradiation nozzle can be moved vertical on an arch-like a path.

Preferably, the irradiation nozzle swivel axis is horizontal. More preferably the cantilever arm swivel axis is horizontal. Further preferably the beam is deflected in the first deflector and second deflector by 90° such that the beam direction between the first and second deflector is perpendicular to the cantilever arm swivel axis and to the irradiation nozzle swivel axis. This allows a particular simple set-up, wherein the cantilever arm is rotated in a vertical plane and wherein both, the beam entering the cantilever arm, and the beam entering the irradiation nozzle are horizontal.

In another preferred aspect, the vertical movement of the irradiation nozzle is effected by a telescope arm. The telescope arm is part of the beam transport system transporting the beam from the beam source to the irradiation nozzle which forms the end portion of the telescope arm. The telescope arm comprises beam guidance means for guiding the beam from the entrance into the telescope arm to irradiation nozzle. The telescope arm comprises a telescope section of variable length. At the downstream end of the telescope section, the beam is guided into a deflector which deflects the beam into the irradiation nozzle. The telescope section of the telescope arm is arranged in such way that the irradiation nozzle moves vertically when the length of the telescope section is varied.

Preferably, the telescope arm and the telescope section are vertical, and the nozzle swivel axis is horizontal. More preferably, the beam enters into the telescope arm in horizontal direction and is deflected into the preferably vertical telescope section with a further deflector. This preferred arrangement again allows a particular simple set-up.

In another preferred aspect, the vertical movement of the irradiation nozzle is effected by arranging the beam source and the beam guidance means guiding the beam into the irradiation nozzle and the irradiation nozzle on a platform which is at least moveable vertically.

In another preferred aspect, the device comprises upstream from the irradiation nozzle a beam deflector allowing to deflect the beam to variable inclinations compared to the horizontal plane. This way, it is possible to vary the vertical elevation of the beam downstream from the aforementioned deflector and to reach the irradiation nozzle in positions of different vertical elevation. More preferably, a further deflector can be positioned downstream from the aforementioned deflector and upstream from the irradiation nozzle, whereby this further deflector is positioned and deflects the beam in such way that the beam enters into the irradiation nozzle in horizontal direction in the various vertical elevations of the irradiation nozzle. Even more preferably, the further deflector follows the vertical movement of the irradiation nozzle, for example by being mechanically coupled to the entrance region of the irradiation nozzle.

The irradiation method according to the invention comprises placing the irradiation object onto a support which is moveable at least horizontally. The method further comprises irradiating a charged particle beam from an irradiation nozzle towards the irradiation object. The beam, which may be generated by a known beam source and guided to the irradiation nozzle by suitable beam guidance means, is fed into the irradiation nozzle and deflected within the irradiation nozzle. According to the invention, the irradiation object is irradiated from various angular directions and the angular direction of the beam impinging onto the irradiation object is varied by moving the support and by moving the irradiation nozzle vertically and rotating it around a nozzle swivel axis, along which the beam enters into the irradiation nozzle.

In a preferred aspect of this method, the distance from the irradiation nozzle to the irradiation object is maintained constant while the angular direction of the beam impinging onto the irradiation object is changed by vertically moving and/or rotating the irradiation nozzle and/or horizontally moving the support.

Figure 9:
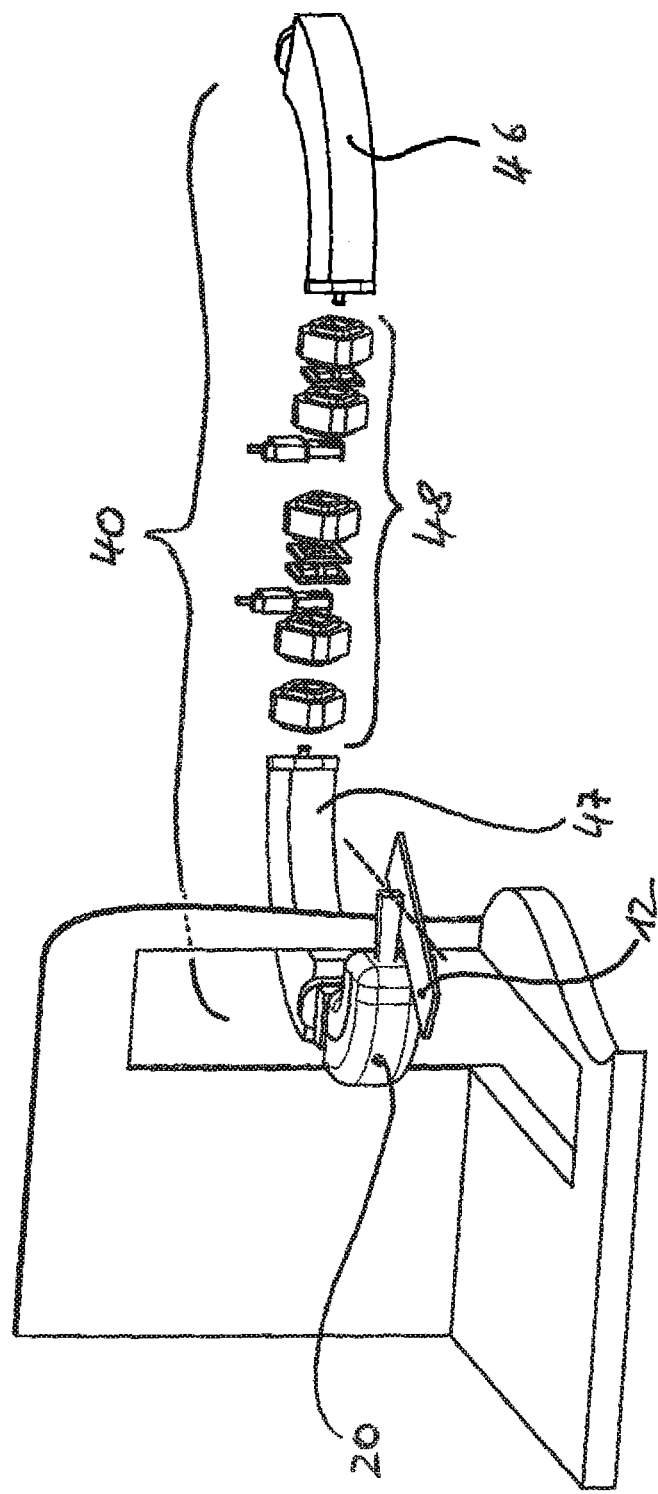
Figure 10:
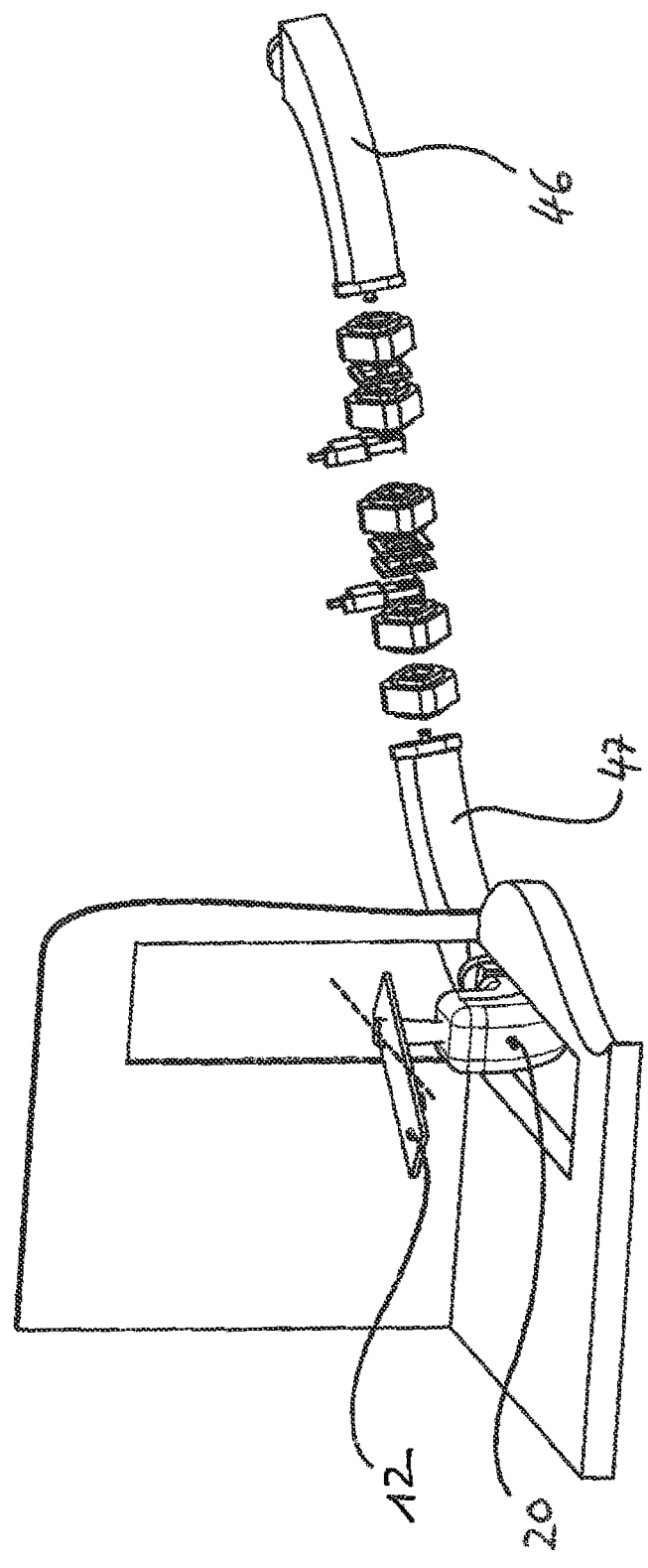

Preferred embodiments of the invention will now be explained in detail below with reference to the figures, in which:

FIG. 1: shows, in a perspective view, an irradiation device according to the invention, FIG. 2: shows the irradiation device of FIG. 1 irradiating from above (0°-position), FIG. 3: shows the irradiation device of FIG. 1 irradiating from 45°-position, FIG. 4: shows the irradiation device of FIG. 1 irradiating from the side (90°-position), FIG. 5: shows the irradiation device of FIG. 1 irradiating from below (180°-position), FIG. 6: shows the irradiation device of FIG. 1 irradiating from −45°-position, FIG. 7: shows in a sequence irradiation from various angular directions between −180° and 0° and 180°, FIG. 8: shows an embodiment of the invention with the irradiation nozzle mounted to a cantilever arm, the cantilever arm being in an upper position, FIG. 9: shows a further view of the embodiment with the cantilever arm, the cantilever arm being in an intermediate position, FIG. 10: shows a further view of the embodiment with the cantilever arm, the cantilever arm being in a lower position, FIG. 11: shows an embodiment of the invention with the irradiation nozzle mounted to a telescope arm, the telescope arm being in an upper position, FIG. 12: shows a further view of the embodiment with the telescope arm, the telescope arm being in an intermediate position, FIG. 13: shows a further view of the embodiment with the telescope arm, the telescope arm being in a lower position, FIG. 14: shows an embodiment of the invention with the irradiation nozzle mounted to a lifting platform, the lifting platform being in an upper position, FIG. 15: shows a further view of the embodiment with the lifting platform, the lifting platform being in an intermediate position, FIG. 16: shows a further view of the embodiment with the lifting platform, the lifting platform being in a lower position, FIG. 17: shows an embodiment of the invention where the beam is directed to variable elevations of the irradiation nozzle by variable deflection of the beam, FIG. 18: shows a further view of the embodiment of FIG. 17, with the irradiation nozzle being in an intermediate position, FIG. 19: shows a further view of the embodiment of FIGS. 17 and 18, with the irradiation nozzle in a lower position.

FIG. 1 shows a perspective view on an irradiation device 10 according to the invention for use in particle therapy. The device comprises a support 12 for the irradiation object, for example a patient support in case of particle therapy. As indicated by the arrow 14, the support 12 can be moved left and right in horizontal direction, parallel to the back wall 16 and the floor 18 of the room in which the irradiation object is irradiated, i. e. the treatment room in case of particle therapy. The irradiation device 10 further comprises an irradiation nozzle 20 irradiating charged particle beam 30, for example a proton beam, towards the support 12 for the irradiation object. The particle beam enters the irradiation nozzle at the entrance side 22 in horizontal direction, along the horizontal nozzle swivel axis 24. Within the irradiation nozzle, the particle beam 30 is deflected by 90° and exits from the irradiation nozzle 20 at the exit side 26 in a direction perpendicular to the nozzle swivel axis 24. As indicated by the arrow 28, the nozzle 20 can be rotated around the nozzle swivel axis 24 and additionally, as indicated with the arrow 29 moved vertically, in such way that the nozzle swivel axis 24 can be lifted and lowered. When the nozzle is rotated around the nozzle swivel axis 24, the beam exiting from the irradiation nozzle describes a vertical plane.

As shown in FIGS. 2 to 6 this allows to irradiate the irradiation object 13, i. e. a patient in case of particle therapy, from all angular directions. The irradiation nozzle 20 can be rotated all around its nozzle swivel axis 24 to all angular positions from −180° to +180°. Additionally, the irradiation nozzle can be moved vertically from positions above the support 12 to positions below the support 12. The support can be moved horizontally, parallel to the back wall 16 of the room, left and right from the vertical path of the nozzle swivel axis 24. This allows a sideward positions of the nozzle 20 with respect to the irradiation object, and the nozzle 20 can pass the support on its vertical path.

Figure 2:
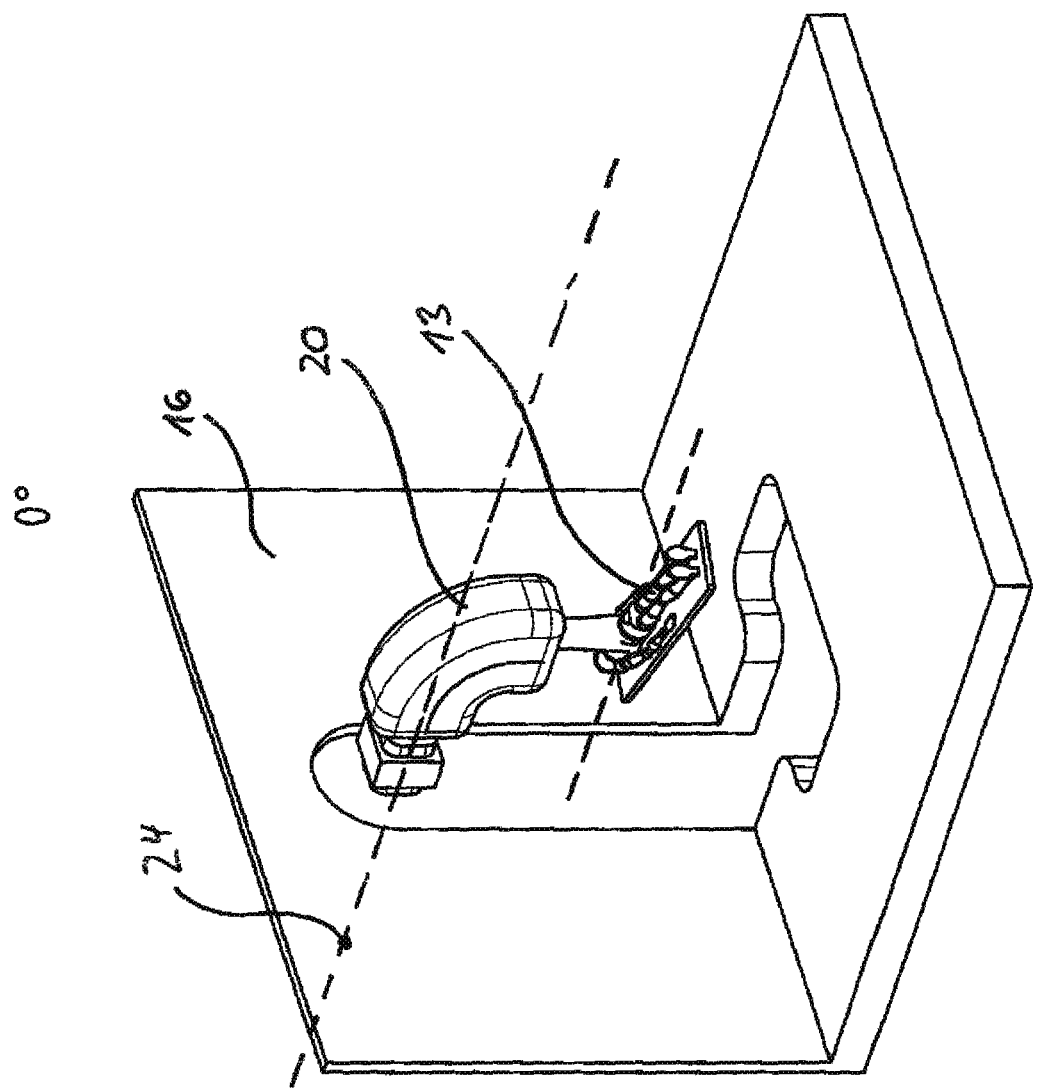

In FIG. 2 the irradiation object 13 is irradiated from straightly above, which is the 0°-position. In FIG. 3 the support 12 with the irradiation object 13 has been moved to the left hand side. The irradiation nozzle has been moved downwards and rotated clock-wise around its swivel axis to the 45°-position. The horizontal movement of the support 12 and the vertical and rotary movement of the nozzle 20 are coordinated in such way that the particle beam 30 impinges onto the irradiation object 13 at the same distance from the irradiation nozzle as in 0°-position, but from an angular direction of 45° with respect to the vertical position.

Figure 4:
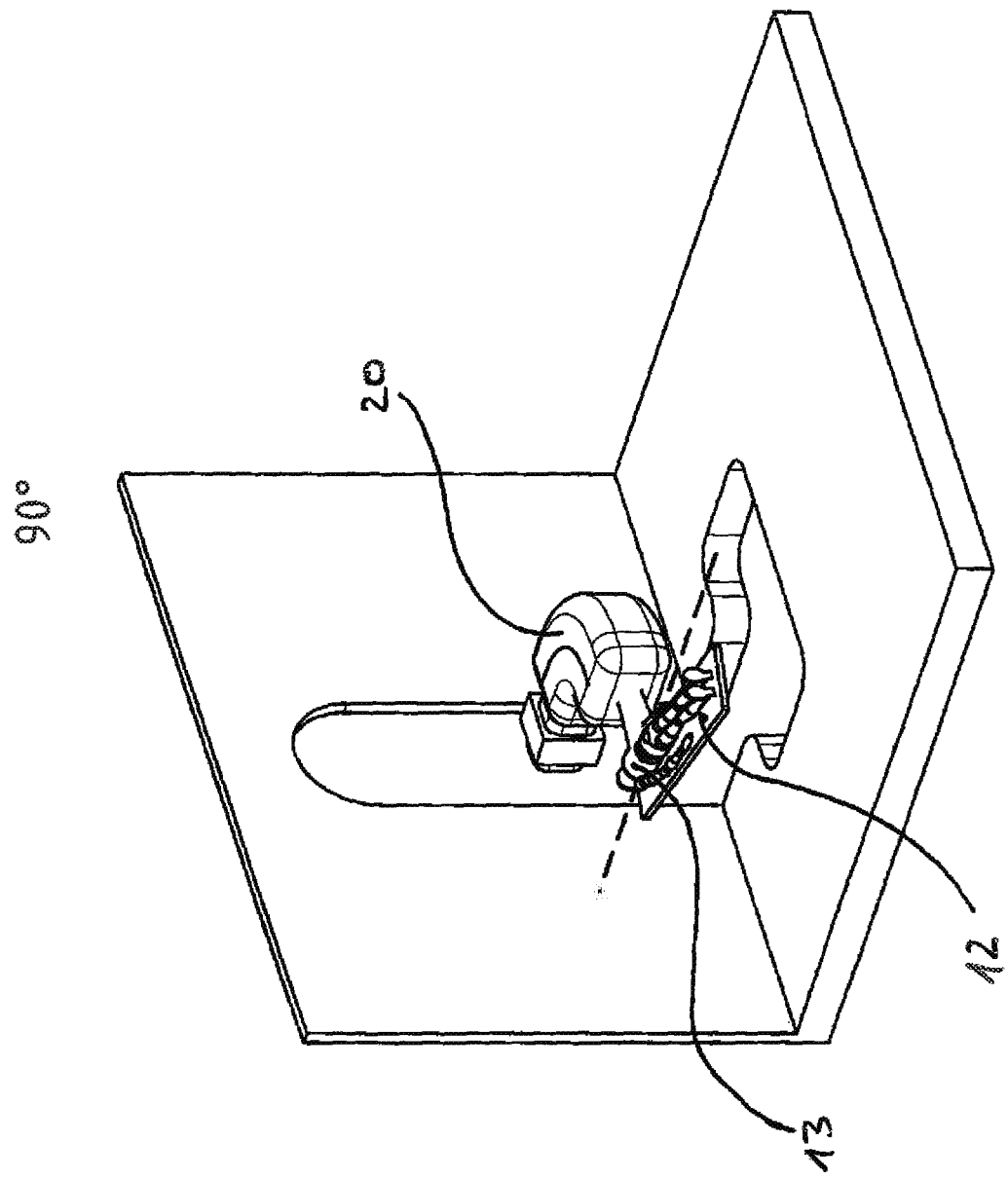

In FIG. 4 the support 12 has been moved further to the left hand side, and the nozzle 20 has been further lowered and further rotated clock-wise around its swivel axis 24 in such a way that the irradiation object 13 is now irradiated from a horizontal direction (90°-position) but at the same distance from the irradiation nozzle as in the 0°- and 45°-position.

Figure 5:
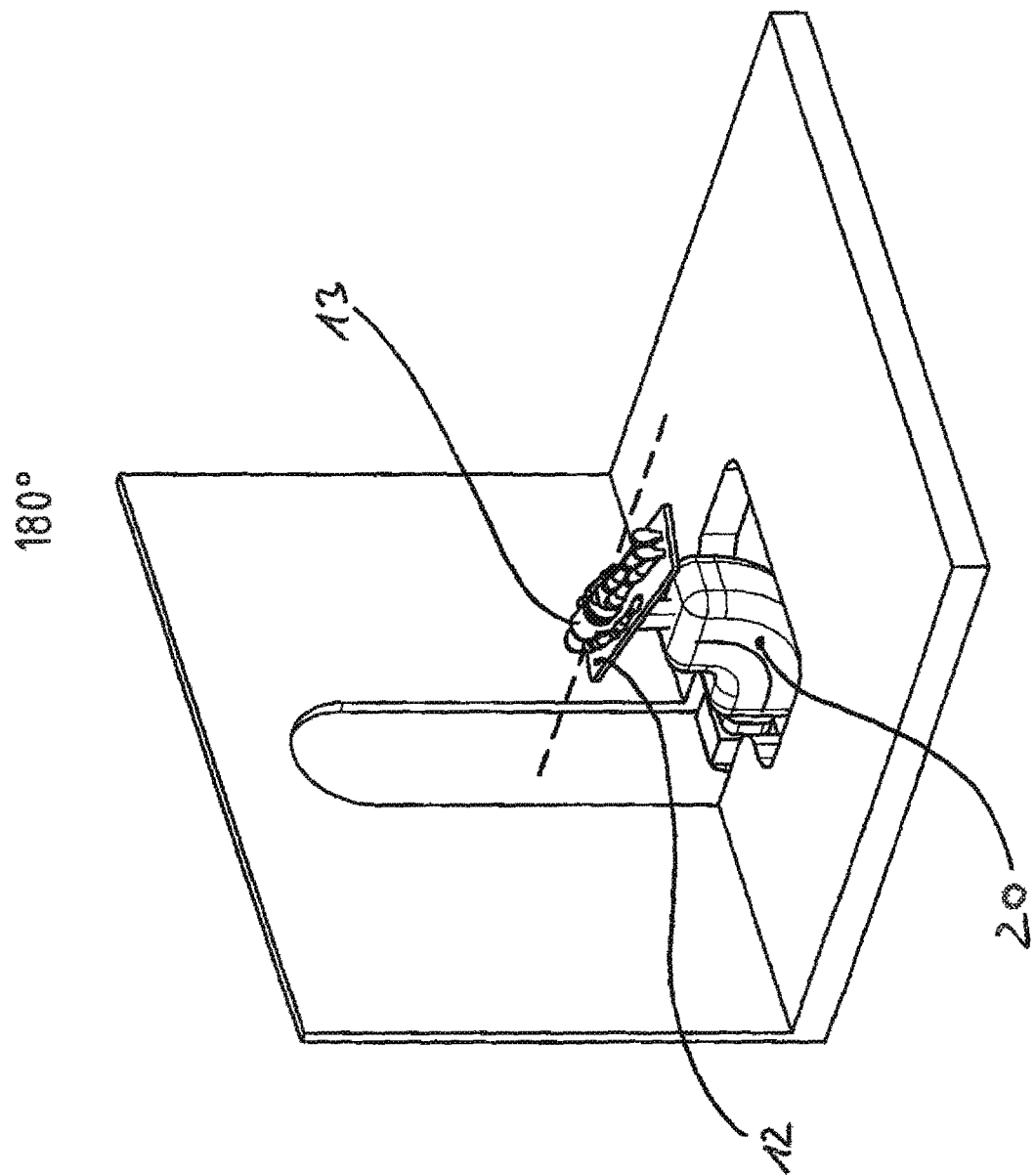

In FIG. 5, the support 12 has been moved back to its central position on the vertical path of the irradiation nozzle 20. The irradiation nozzle has been moved downwards to its lower most position, which is partly below the floor 18 of the treatment room, and rotated in such way that the beam irradiates straight upwards from the nozzle. When moving into the 180°-position shown in FIG. 5, the movements of the support and the irradiation nozzle have been coordinated in such way that the irradiation object 13 is irradiated from straight below, but at the same distance from the nozzle 20 as in the irradiation positions shown in FIGS. 2 to 4.

Figure 3:
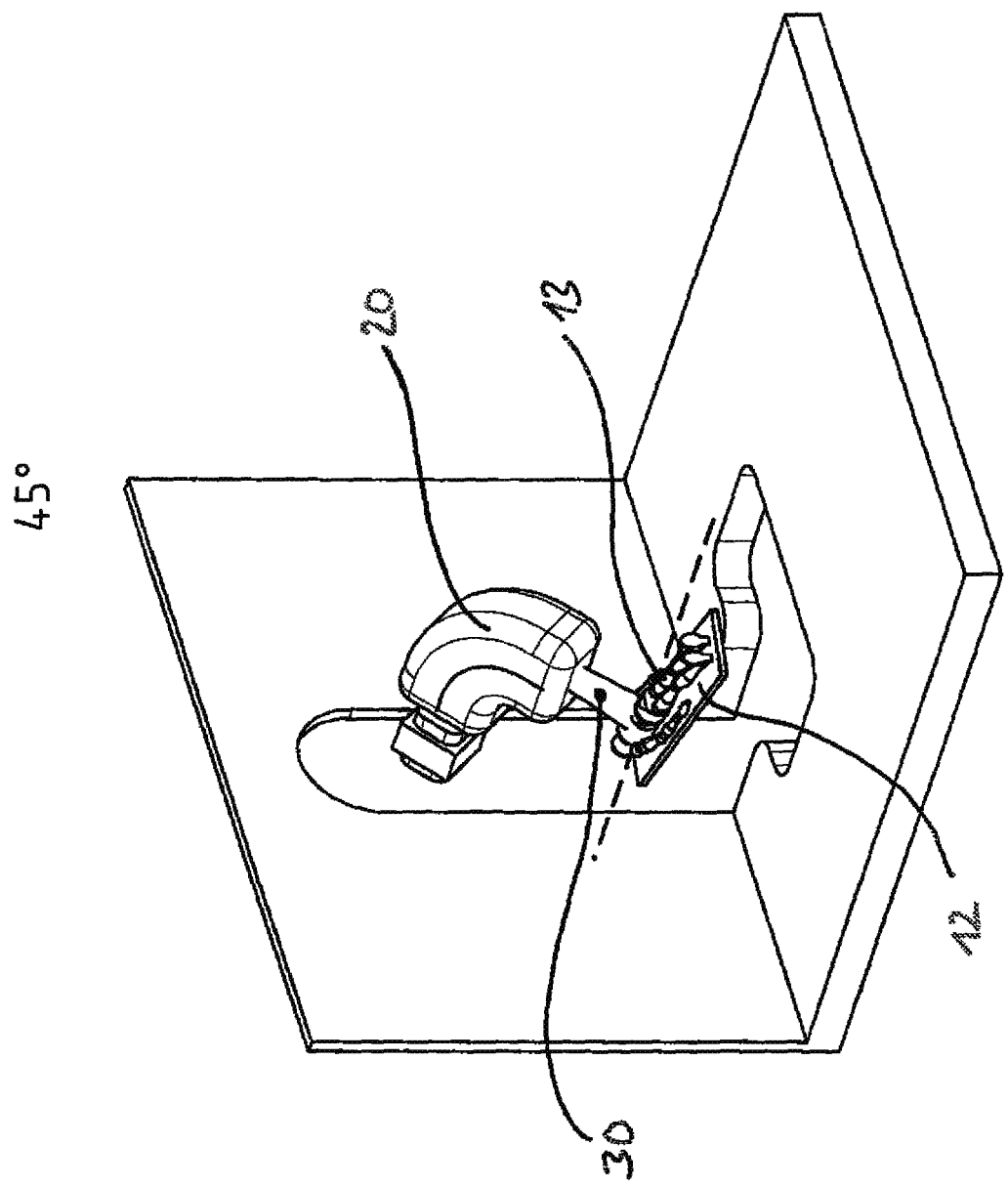
Figure 6:
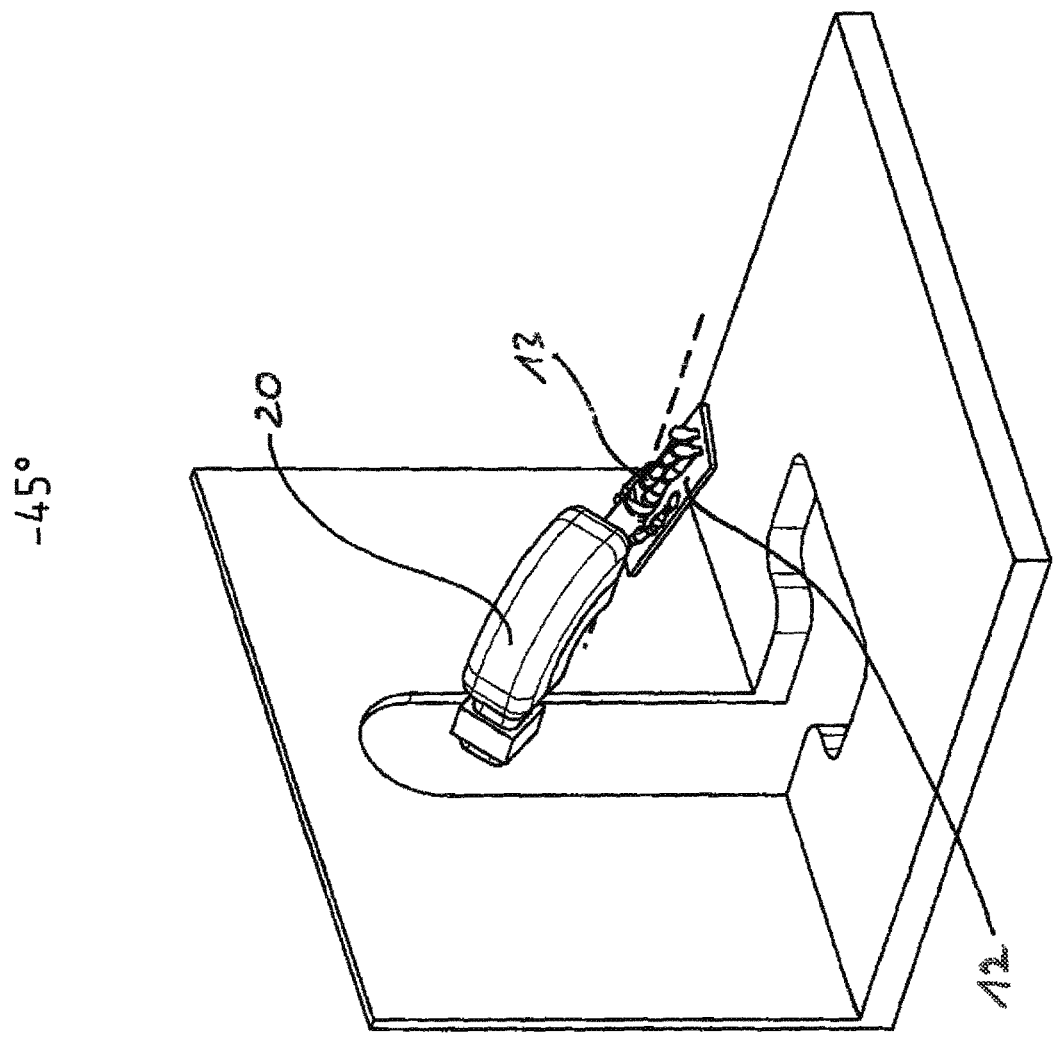

In FIG. 6, the support 12 has been moved in the opposite direction as in FIG. 3, to the right hand side from the vertical path of the irradiation nozzle 20. The irradiation nozzle has been moved to the same vertical position as in FIG. 3, but rotated counter-clockwise by −45° compared to the 0°-position. In the −45°-position shown in FIG. 6 the irradiation object 13 is irradiated from an angular direction of for −45° compared to the vertical direction, but at the same distance from the irradiation nozzle.

FIG. 7 shows an overview of the sequence of irradiation positions 0°, 45°, 90°, 135°, 180°, −45°, −90° and −135°. By suitable movement of the support 12 and the irradiation nozzle 20, the irradiation object 13 can be irradiated from all angular directions at the same distance from the irradiation nozzle. By moving the support 12 length wise along the dashed line 32 shown in FIG. 1 the irradiation location can be shifted along the body of a patient 13.

Figure 8:
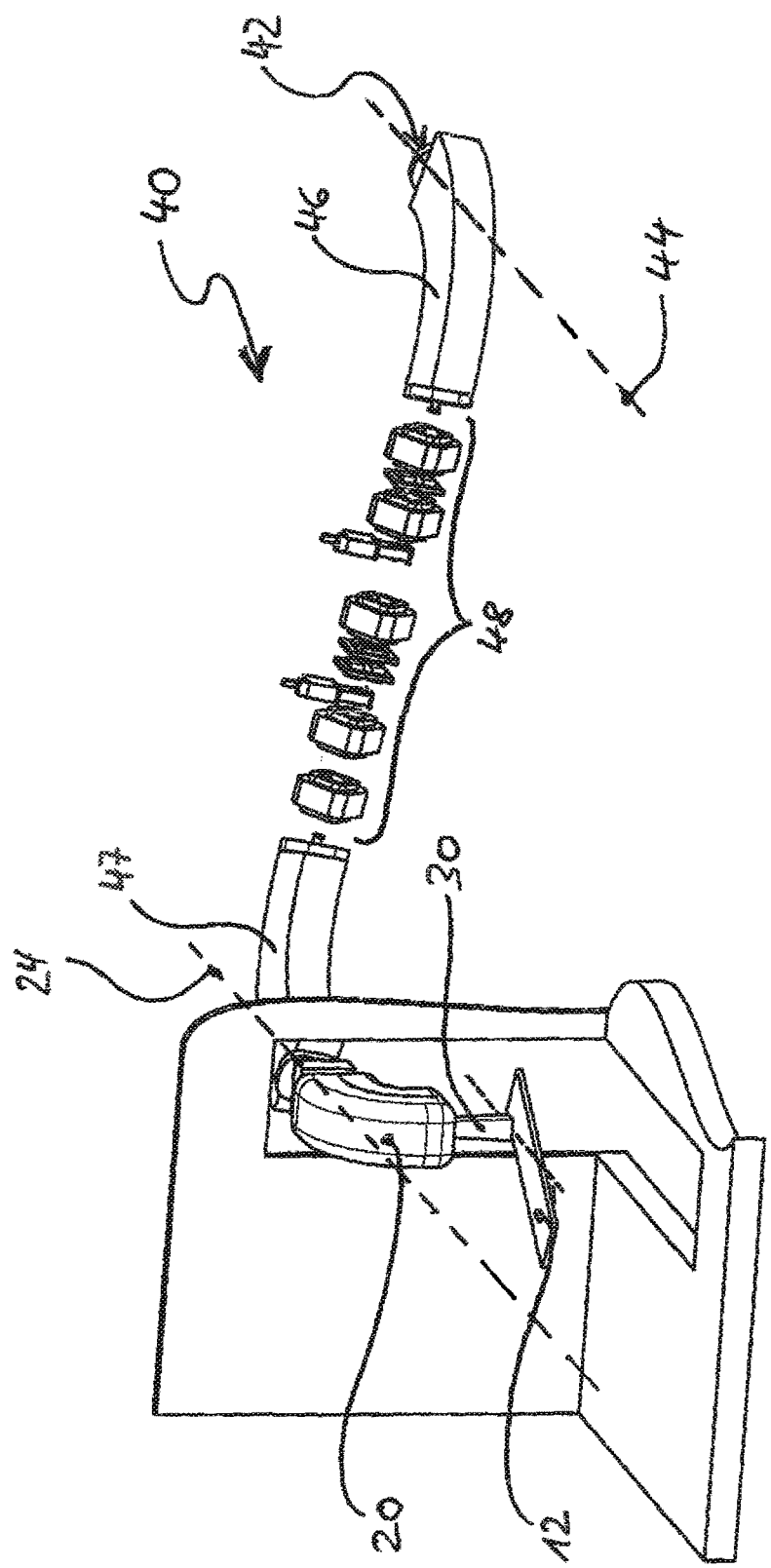

FIG. 8 shows an embodiment of the invention wherein the vertical movement of the irradiation nozzle 20 is effected by a pivotable cantilever arm 40. The particle beam 30 enters into the cantilever arm 40 at the entrance side 42 along the cantilever arm swivel axis 44. The cantilever arm comprises beam guidance means 46, 47, 48 guiding the beam 30 to the nozzle 20. The nozzle 20 forms the end portion of the cantilever arm 40 and is pivotably mounted to the cantilever arm. The cantilever arm swivel axis 44 and the nozzle swivel axis 24 are horizontal and parallel. The cantilever arm 40 comprises a first beam deflector 46 which deflects the particle beam entering into the cantilever arm away from the cantilever arm swivel axis 44 by 90°, into a direction perpendicular to the cantilever arm swivel axis 44. From the first beam deflector 46 the beam 30 is guided by further beam guidance means 48 to a second beam deflector 47 deflecting the beam by 90° into the irradiation nozzle 20 along the nozzle swivel axis 24. As shown in FIGS. 8 to 10 the irradiation nozzle 20 can be moved vertically on an arch-like a path by swivelling the cantilever arm 40 around the cantilever arm swivel axis 44. By suitable coordinating the swivelling of the cantilever arm 40 with the rotary movement of the irradiation nozzle 20 around the nozzle swivel axis 24 and the horizontal movement of the support 12, an irradiation object on the support 12 can be irradiated from all angular directions around the support 12. For example, as shown in FIG. 9, an irradiation object can be irradiated horizontally from the side, and as shown in FIG. 10, vertically from straight below. Due to the rotary movement of the cantilever arm around the cantilever arm swivel axis, the movement of the irradiation nozzle is not straightly vertical, but combined with a horizontal movement according to the character of a circular motion. However, by suitable coordination with the horizontal movement of the support and the rotary movement of the irradiation nozzle around the nozzle swivel axis, the horizontal component of the arch-path of the irradiation nozzle can be compensated, and it can be achieved that the irradiation object is irradiated from all angular directions at the same distance from the irradiation nozzle. The cantilever design allows to reduce the space that needs to be shielded for radiation protection reasons compared to known gantry-systems. In the cantilever design the beam line guiding the beam to the irradiation nozzle moves in a plane, whereas in known gantries the beam line to the irradiation nozzle rotates in 3D-space.

Figure 11:
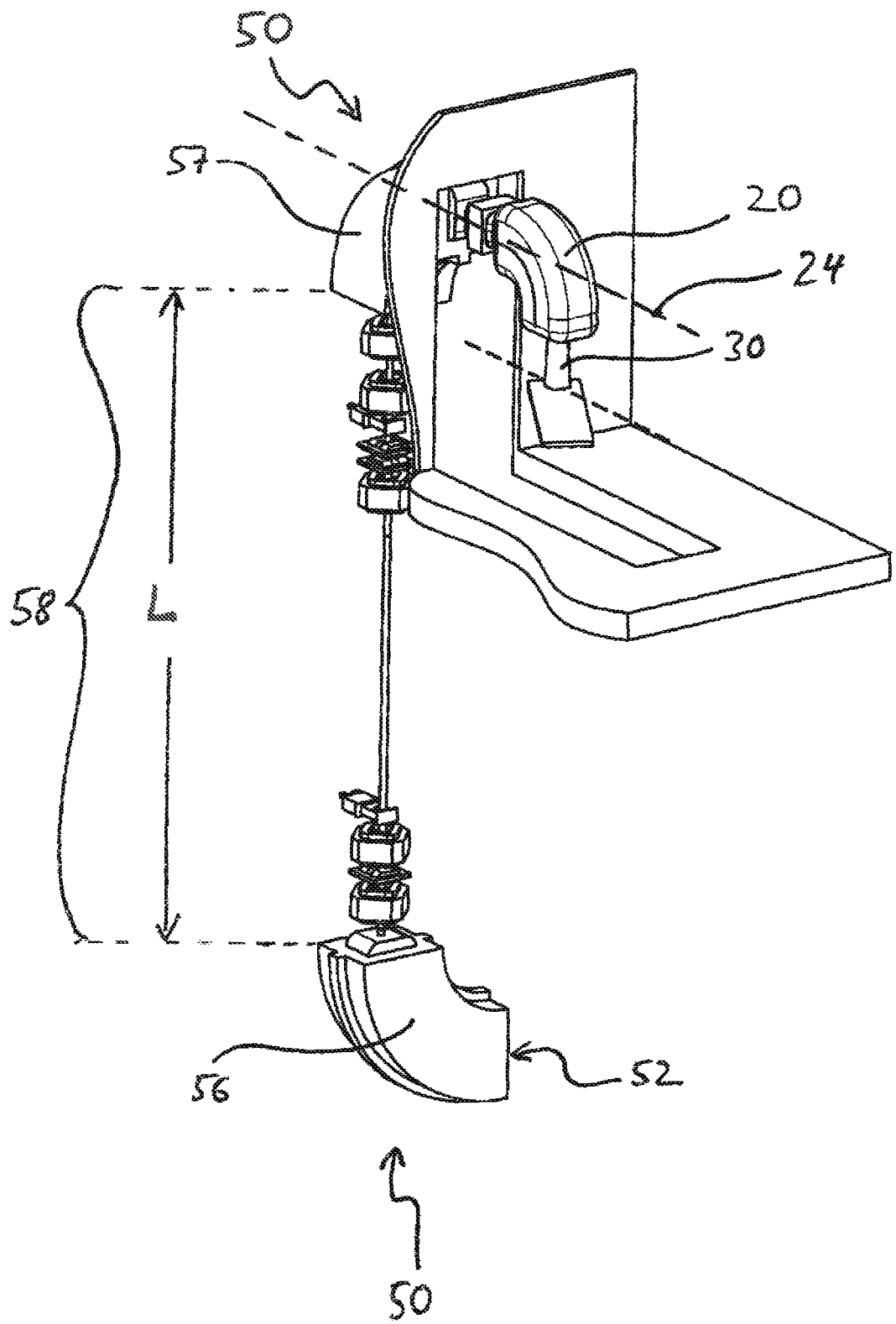
Figure 12:
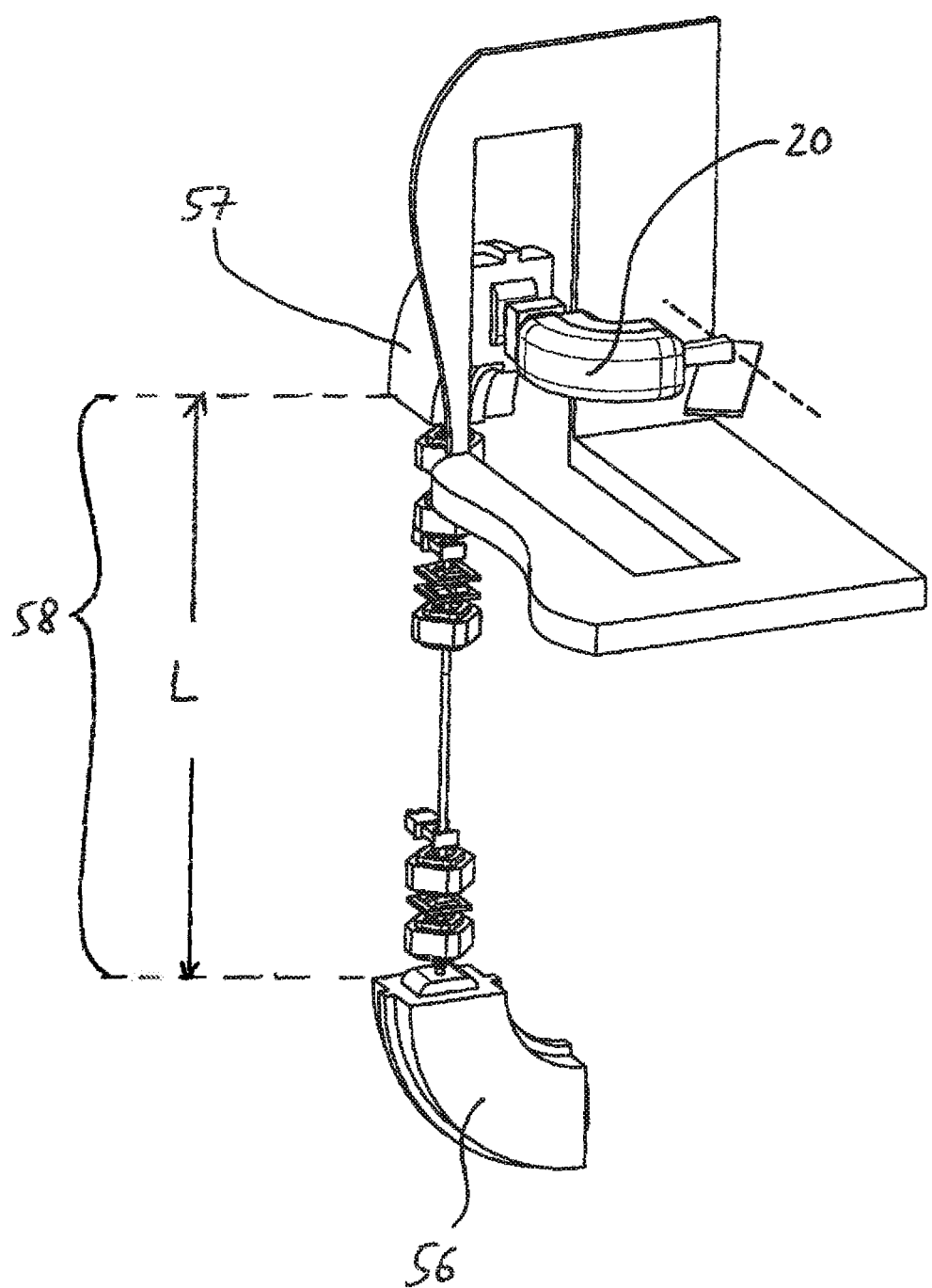
Figure 13:
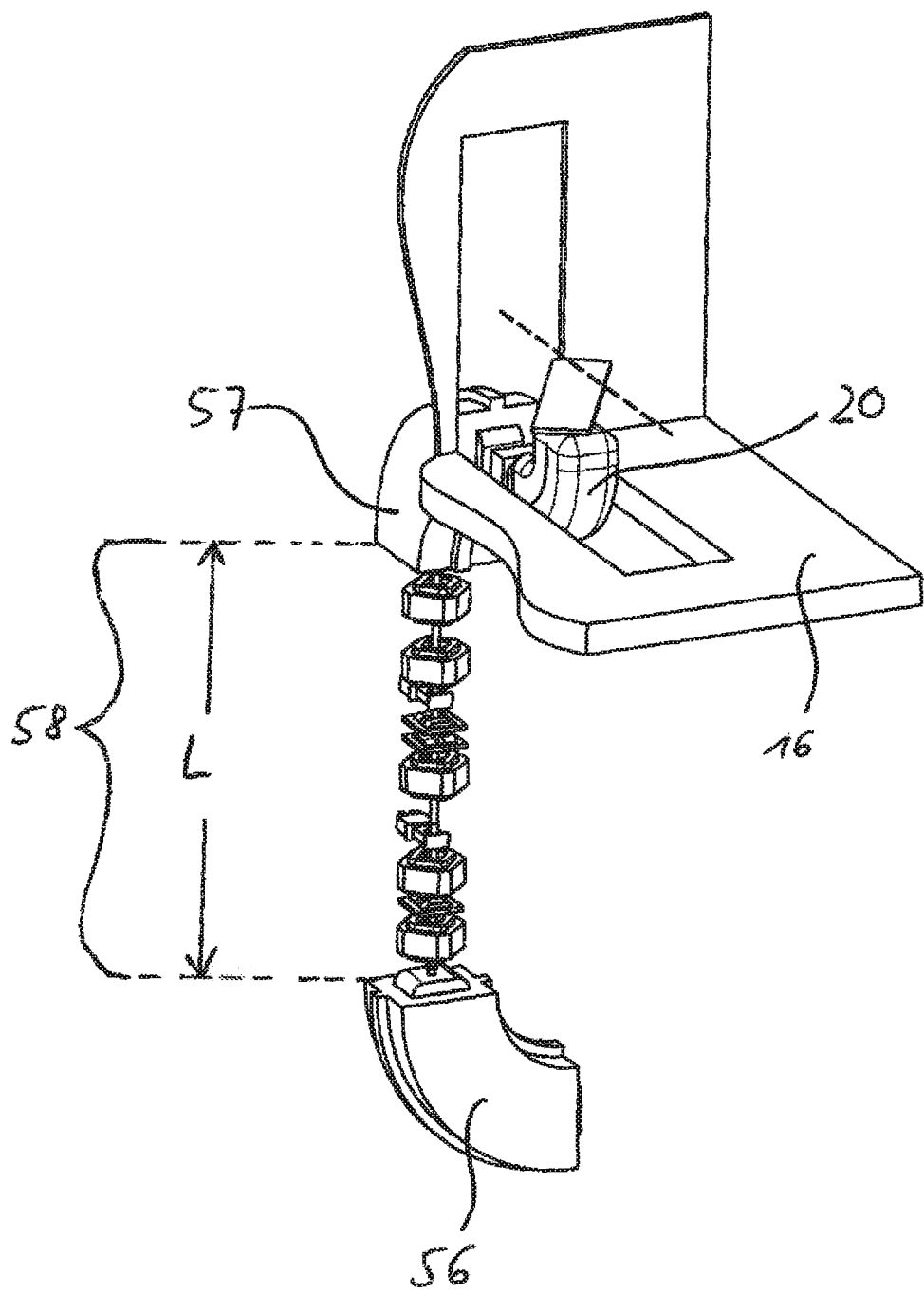

FIGS. 11 to 13 show another preferred embodiment of the invention, wherein the vertical movement of the irradiation nozzle 20 is effected by a telescope arm 50. The telescope arm 50 comprises a telescope section 58 of variable length L. The particle beam 30 enters into the telescope arm 50 on the entrance side 52 in horizontal direction. The telescope arm comprises deflectors 56 and 57. The deflector 56 deflects the beam 30 entering into the telescope arm by 90° into the vertical telescope section 58. Downstream from the telescope section 58 the second deflector deflects 57 the beam 30 into the irradiation nozzle along the horizontal nozzle swivel axis 24. The length L of the telescope section can be varied telescopically, and this way the irradiation nozzle 20 can be moved vertically. In the situation shown in FIG. 11, the telescope section 58 is extended to its maximum length L, and the irradiation object is irradiated from straightly above. In the situation shown in FIG. 12, the length L of the telescope section 58 has been reduced compared to FIG. 11, and the irradiation nozzle 20 is now at a lower position in order to irradiate the irradiation object horizontally from the side. In the situation shown in FIG. 13, the length L of the telescope section 58 has been further reduced compared to FIG. 12 in order to irradiate the irradiation object from straightly below. Also in this embodiment, the horizontal movement of the support 12 and vertical and rotary movement of the irradiation nozzle can be coordinated in such way, that the irradiation object on the support 12 can be irradiated from all angular directions at a defined preferably constant distance. Also the telescope design according to this embodiment allows among other advantages reduce the space that has to be shielded for radiation protection reasons.

Figure 14:
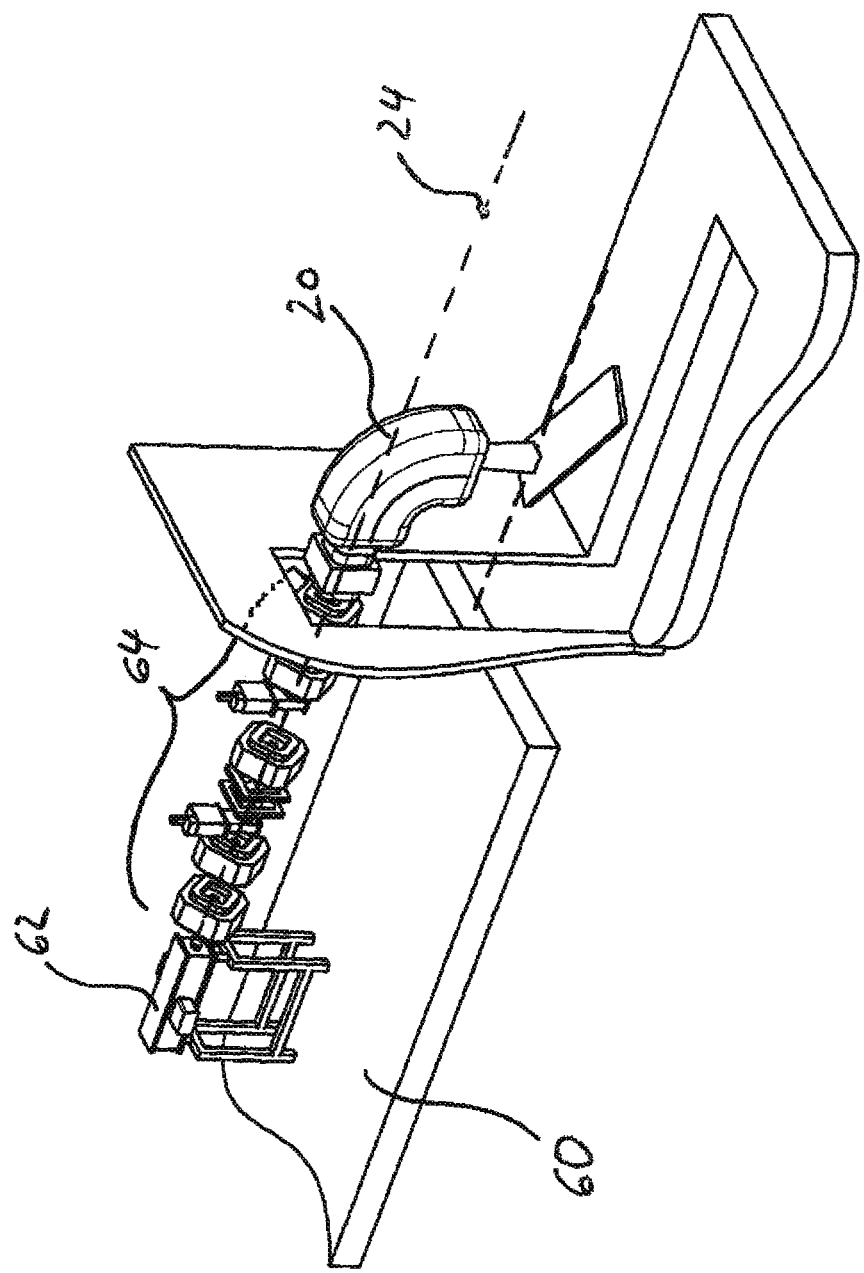
Figure 15:
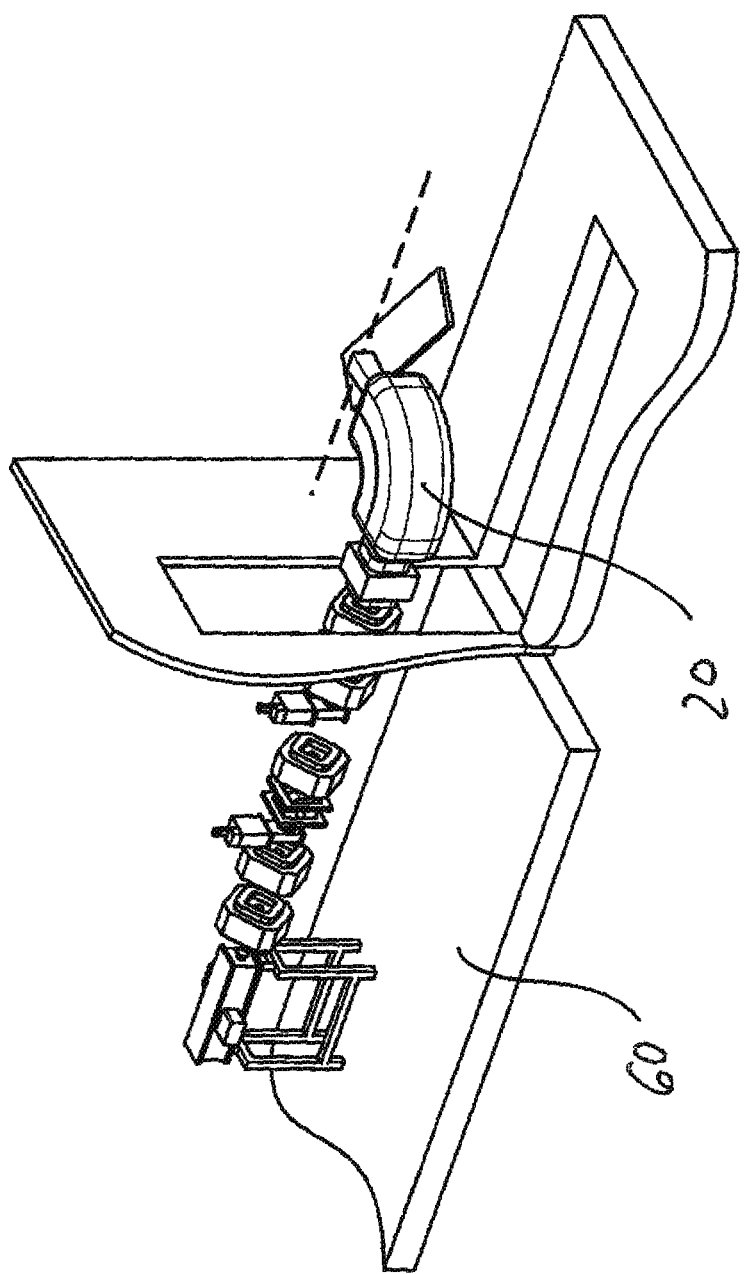
Figure 16:
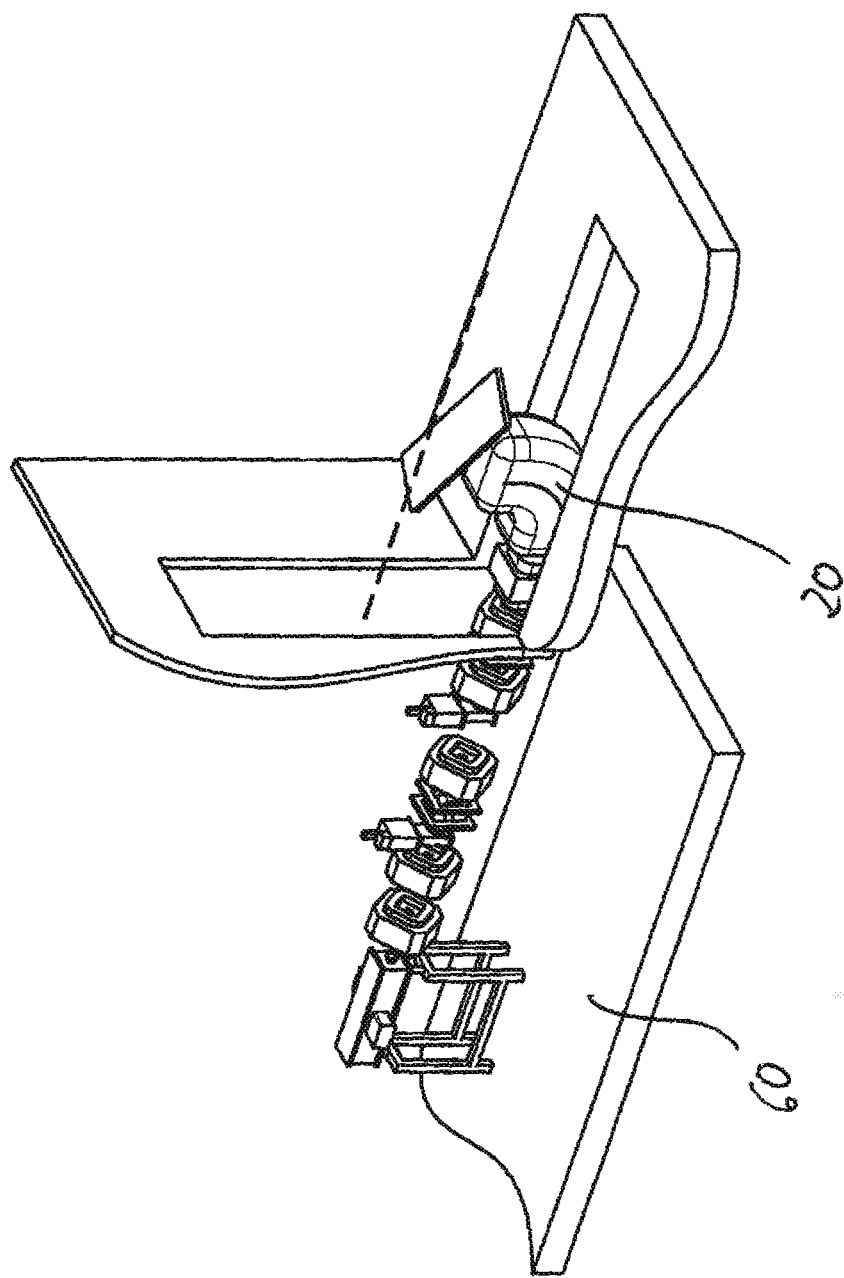

FIGS. 14 to 16 show another preferred embodiment of the invention, wherein the vertical movement of the irradiation nozzle 20 is effected by arranging the beam source 62 generating the particle beam and the beam guidance means 64 guiding the beam to the irradiation nozzle and the irradiation nozzle 20 on a platform 60 which can be moved vertically, i. e. lifted and lowered. In this embodiment the platform 60 is a lifting platform for the beam source and the whole beam transport system up to the irradiation nozzle and also the irradiation nozzle 20 itself. The beam enters into the irradiation nozzle horizontally along the nozzle swivel axis 24. In FIG. 14, the platform 60 and the irradiation nozzle 20 is in an upper position allowing to irradiate the irradiation object from straightly above. In FIG. 15 the lifting platform 60 and the irradiation nozzle 20 is an intermediate position allowing to irradiate the irradiation object horizontally from the side. In FIG. 16 the lifting platform 60 and the irradiation nozzle 20 is a lower position allowing to irradiate the irradiation object from straight below. Again, by coordinating the vertical movement of the platform 60 and the rotary movement of the irradiation nozzle 20 and the horizontal movement of the support 12, it can be achieved that an irradiation object is irradiated from all angular directions at a defined distance.

Figure 17:
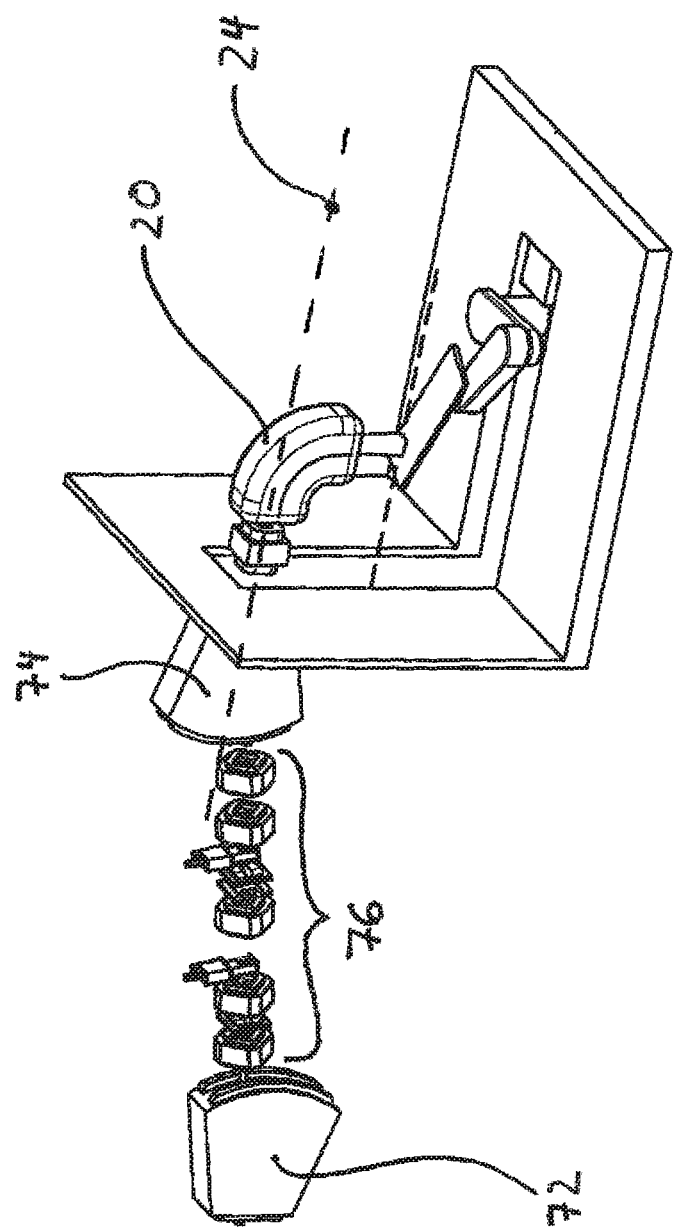
Figure 18:
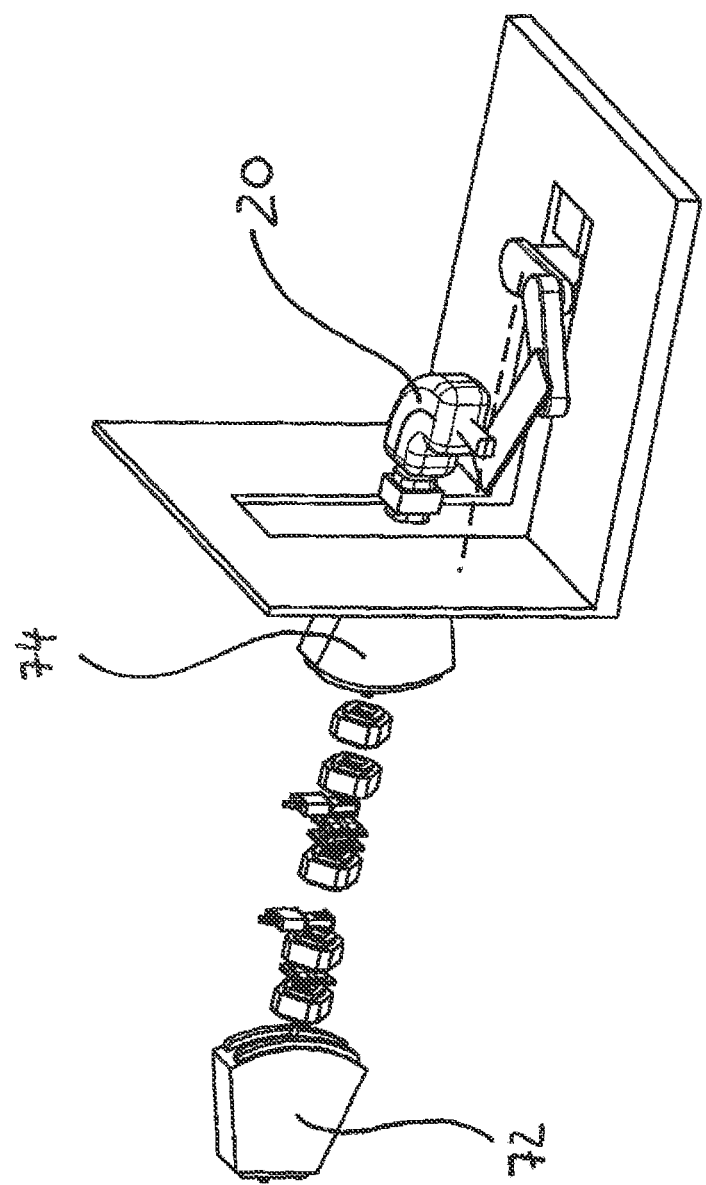
Figure 19:
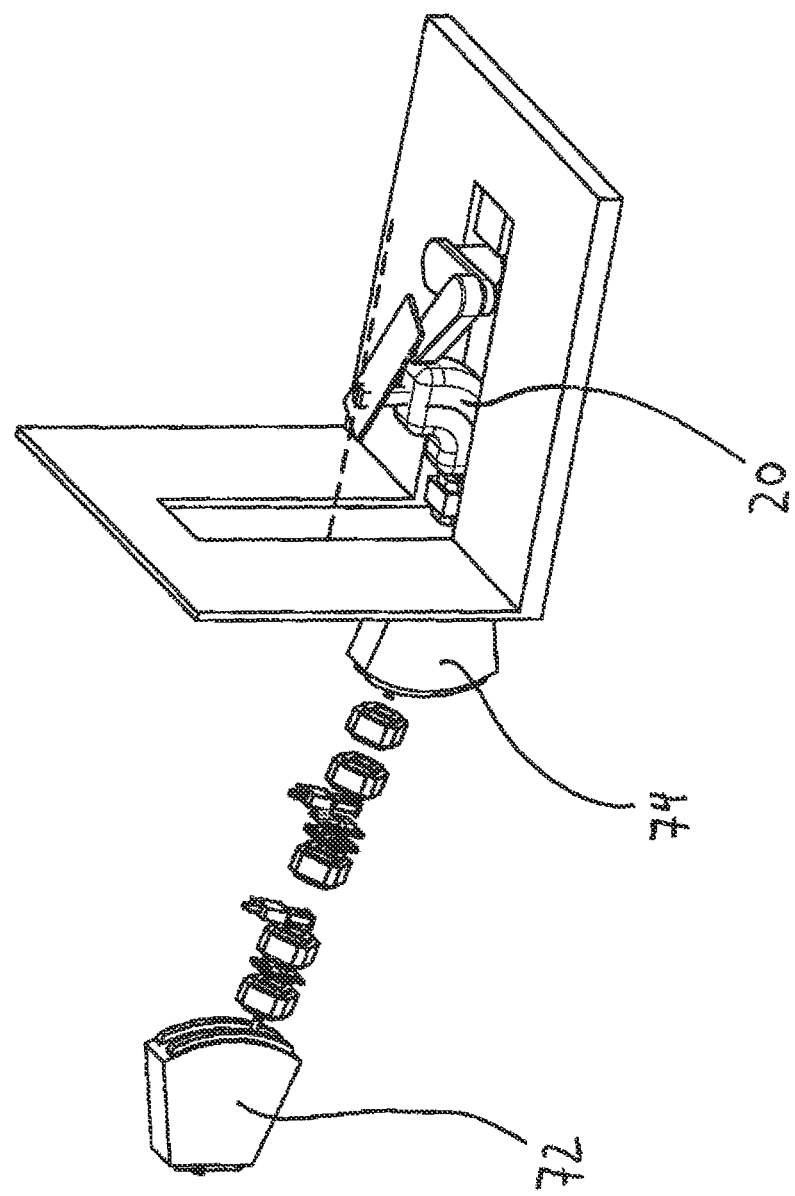

FIGS. 17 to 19 show another preferred embodiment of the invention, wherein a first deflector 72 is positioned upstream from the irradiation nozzle 20. The beam enters into the first deflector 72 in horizontal direction which allows to deflect the beam to variable inclinations compared to the horizontal plane. By varying the inclination it is possible to reach various vertical elevations of the beam downstream from the first deflector 72. This way, the beam can follow the vertical movement of the irradiation nozzle 20 by varying the deflection of the beam by the first deflector 72. This embodiment further comprises a second deflector 74 which is positioned on the beam line before the entrance of the beam into the irradiation nozzle and which follows the vertical movement of the irradiation nozzle. The second deflector 72 deflects the beam in such way that it enters the irradiation nozzle in horizontal direction. Further beam guidance means 76 are positioned on the beam line between the first deflector 72 and the second deflector 74. In FIG. 17, the irradiation nozzle 20 is an upper position allowing to irradiate the irradiation object from straightly above. The beam is deflected by the first deflector 72 upwards so as to enter into the second deflector 74 which brings the beam into horizontal direction and directs the beam into the irradiation nozzle 20 along the horizontal nozzle swivel axis 24. In FIG. 18, the irradiation nozzle 20 is an intermediate position allowing to irradiate the irradiation object horizontally from the side. The beam leaves the first deflector 72 in horizontal direction and passes through the second deflector 74 so as to enter the irradiation nozzle also in horizontal direction. In FIG. 19, the irradiation nozzle is in a lower position allowing to irradiate the irradiation object from straight below. In this position, the beam is deflected by the first deflector 72 downwards in order to reach the second deflector 74 and the irradiation nozzle in the lower position. Also in this embodiment, by coordinating the vertical and the rotary movement of the irradiation nozzle 20 and the inclination of the beam leaving the first deflector 72, it can be achieved that an irradiation object is irradiated from all angular directions at a defined, preferably constant, distance.

The embodiments described above provide various advantages compared to known gantry designs.

Optionally, the support for the irradiation object can be moved vertically, either by moving the support itself relatively to the room floor, or by elevating and lowering the room floor with the support placed thereon. The vertical movement of the support may be combined with a horizontal movement of the support and/or a rotary movement of the support around a vertical axis and/or a vertical and/or rotary movement of the nozzle. A suitable combination of such movements may be used for example for advantageous irradiation treatment plans and/or for avoidance of collision between nozzle and irradiation object or support. With the support being moveable vertically, it is also possible to irradiate the irradiation objects from various and/or all angular directions without moving the irradiation nozzle vertically, by suitable combination of rotary movement of the irradiation nozzle and horizontal and/or vertical and/or rotary movement around a vertical axis of the support.

The invention claimed is:

1. An irradiation device for irradiating an irradiation object with heavy charged particles, comprising:
   a support for the irradiation object; and
   an irradiation nozzle irradiating a charged particle beam towards the irradiation object,
   wherein the particle beam is deflected within the irradiation nozzle,
   wherein the support for the irradiation object is moveable at least horizontally, and
   wherein the irradiation nozzle is moveable at least vertically and is independently rotatable around a nozzle swivel axis along which the particle beam enters into the irradiation nozzle.

2. The irradiation device according to claim 1, wherein the nozzle swivel axis is horizontal.

3. The irradiation device according to claim 2, wherein the vertical and the rotary movements of the irradiation nozzle are coordinated by a control device controlling position and direction of the particle beam irradiated from the irradiation nozzle.

4. The irradiation device according to claim 2, wherein at least two of the three movements
(iv) horizontal movement of the support
(v) vertical movement of the irradiation nozzle
(vi) rotary movement of the irradiation nozzle
are coordinated by a control device in such a way that the particle beam keeps impinging onto the irradiation object when the support and/or the irradiation nozzle is moved.

5. The irradiation device according to claim 1, wherein the vertical and the rotary movements of the irradiation nozzle are coordinated by a control device controlling position and direction of the particle beam irradiated from the irradiation nozzle.

6. The irradiation device according to claim 1, wherein at least two of the three movements
(i) horizontal movement of the support
(ii) vertical movement of the irradiation nozzle
(iii) rotary movement of the irradiation nozzle
are coordinated by a control device in such a way that the particle beam keeps impinging onto the irradiation object when the support and/or the irradiation nozzle is moved.

7. The irradiation device according to claim 1, wherein the horizontal movement of the support and the vertical and rotary movements of the irradiation nozzle are coordinated by a control device in such a way that the particle beam impinges onto the irradiation object at a defined distance from the irradiation nozzle when the support and/or the irradiation nozzle is moved.

8. The irradiation device according to claim 1, wherein an angle between a direction of the particle beam impinging onto the irradiation object and the vertical direction can be varied between 0° and +180°.

9. The irradiation device according to claim 1, wherein the support for the irradiation object is rotatable around a vertical axis by 180°.

10. The irradiation device according to claim 1, further comprising:
a pivotable cantilever arm for effecting the vertical movement of the irradiation nozzle, the cantilever arm being pivotable around a cantilever arm swivel axis and comprising a beam guidance device guiding the particle beam to the irradiation nozzle forming an end portion of the cantilever arm,
wherein the particle beam enters into the cantilever arm along the cantilever arm swivel axis,
wherein the cantilever arm comprises a first beam deflector deflecting the entering particle beam away from the cantilever arm swivel axis by 90°, and
wherein the cantilever arm comprises, downstream from the first deflector, a second deflector deflecting the particle beam into the irradiation nozzle.

11. The irradiation device according to claim 10, wherein the cantilever arm swivel axis and/or the nozzle swivel axis is horizontal and/or the first deflector and/or the second deflector deflect the particle beam by 90°.

12. The irradiation device according to claim 1, further comprising a telescope arm for effecting vertical movement of the irradiation nozzle,
the telescope arm comprising a beam guidance device for guiding the particle beam to the irradiation nozzle forming an end portion of the telescope arm,
wherein the telescope arm comprises a telescope section of variable length (L) and, at a downstream end of the telescope section, a deflector deflecting the particle beam into the irradiation nozzle,
wherein the irradiation nozzle is moved vertically by variation of the length (L) of the telescope section.

13. The irradiation device according to claim 12, wherein the nozzle swivel axis is horizontal and/or the particle beam enters into the telescope arm in horizontal direction and is deflected into the telescope section.

14. The irradiation device according to claim 12, wherein the nozzle swivel axis is horizontal and/or the particle beam enters into the telescope arm in horizontal direction and is deflected into the telescope section, which is vertical.

15. The irradiation device according to claim 1, wherein the vertical movement of the irradiation nozzle is effected by arranging a particle beam source, a beam guidance device guiding the particle beam into the irradiation nozzle, and the irradiation nozzle on a platform, the platform being at least movable vertically.

16. The irradiation device according to claim 1, further comprising, upstream from the irradiation nozzle, a particle beam deflector allowing to deflect the particle beam to variable inclinations compared to a horizontal plane in such a way that the particle beam can enter into the irradiation nozzle at various vertical elevations.

17. The irradiation device according to claim 1, wherein the horizontal movement of the support and the vertical and rotary movements of the irradiation nozzle are coordinated by a control device in such a way that the particle beam impinges onto the irradiation object at a defined, constant distance from the irradiation nozzle when the support and/or the irradiation nozzle is moved.

18. The irradiation device according to claim 1, wherein an angle between a direction of the particle beam impinging onto the irradiation object and the vertical direction is configured to be varied between −180° and +180°.

19. The irradiation device according to claim 1, wherein an angle between a direction of the particle beam impinging onto the irradiation object and the vertical direction can be continuously varied between 0° and +180°.

20. The irradiation device of claim 1, wherein the particle beam is deflected within the irradiation nozzle by 90°.

21. A method for irradiating an irradiation object with heavy charged particles from various angular directions, comprising:
placing the irradiation object onto a support, which is moveable at least horizontally;
irradiating a charged particle beam from an irradiation nozzle along a certain irradiation direction towards the irradiation object;
deflecting the particle beam within the irradiation nozzle; and
changing the irradiation direction by moving the support at least horizontally and by moving the irradiation nozzle at least vertically and rotating the irradiation nozzle around a swivel axis, along which the particle beam enters the irradiation nozzle,
wherein the irradiation nozzle is configured to be independently rotatable around the swivel axis.

22. The method according to claim 21, wherein a distance from the irradiation nozzle to the irradiation object is maintained constant while the irradiation direction is changed by moving and/or rotating the irradiation nozzle and/or moving the support.

23. The method according to claim 21, further comprising coordinating at least two of the three movements
(i) horizontal movement of the support
(ii) vertical movement of the irradiation nozzle
(iii) rotary movement of the irradiation nozzle
in such a way that the particle beam keeps impinging onto the irradiation object when the support and/or the irradiation nozzle is moved.

24. An irradiation device for irradiating an irradiation object with heavy charged particles, comprising:
a support for the irradiation object; and
an irradiation nozzle irradiating a charged particle beam towards the irradiation object,
wherein the particle beam is deflected within the irradiation nozzle,
wherein the support for the irradiation object is moveable at least horizontally, and
wherein the irradiation nozzle is moveable at least vertically and is rotatable around a nozzle swivel axis along which the particle beam enters into the irradiation nozzle,
the irradiation device further comprising:
a pivotable cantilever arm for effecting the vertical movement of the irradiation nozzle, the cantilever arm being pivotable around a cantilever arm swivel axis and comprising a beam guidance device guiding the particle beam to the irradiation nozzle forming an end portion of the cantilever arm,
wherein the particle beam enters into the cantilever arm along the cantilever arm swivel axis, wherein the cantilever arm comprises a first beam deflector deflecting the entering particle beam away from the cantilever arm swivel axis, and
wherein the cantilever arm comprises, downstream from the first deflector, a second deflector deflecting the particle beam into the irradiation nozzle.

25. The irradiation device according to claim 24, wherein the cantilever arm swivel axis and/or the nozzle swivel axis is horizontal and/or the first deflector and/or the second deflector deflect the particle beam by 90°.

26. The irradiation device according to claim 24, wherein the nozzle swivel axis is horizontal.

27. The irradiation device according to claim 24, wherein the vertical and the rotary movements of the irradiation nozzle are coordinated by a control device controlling position and direction of the particle beam irradiated from the irradiation nozzle.

28. The irradiation device according to claim 24, wherein at least two of the three movements
(i) horizontal movement of the support
(ii) vertical movement of the irradiation nozzle
(iii) rotary movement of the irradiation nozzle
are coordinated by a control device in such a way that the particle beam keeps impinging onto the irradiation object when the support and/or the irradiation nozzle is moved.

29. The irradiation device according to claim 24,
wherein the horizontal movement of the support and the vertical and rotary movements of the irradiation nozzle are coordinated by a control device in such a way that the particle beam impinges onto the irradiation object at a defined distance from the irradiation nozzle when the support and/or the irradiation nozzle is moved.

30. The irradiation device according to claim 24,
wherein an angle between a direction of the particle beam impinging onto the irradiation object and the vertical direction can be varied between 0° and +180°.

31. The irradiation device according to claim 24, wherein the support for the irradiation object is rotatable around a vertical axis by 180°.

32. An irradiation device for irradiating an irradiation object with heavy charged particles, comprising:
a support for the irradiation object; and
an irradiation nozzle irradiating a charged particle beam towards the irradiation object,
wherein the particle beam is deflected within the irradiation nozzle,
wherein the support for the irradiation object is moveable at least horizontally, and
wherein the irradiation nozzle is moveable at least vertically and is rotatable around a nozzle swivel axis along which the particle beam enters into the irradiation nozzle,
the irradiation device further comprising:
a telescope arm for effecting vertical movement of the irradiation nozzle, the telescope arm comprising a beam guidance device for guiding the particle beam to the irradiation nozzle forming an end portion of the telescope arm,
wherein the telescope arm comprises a telescope section of variable length (L) and, at a downstream end of the telescope section, a deflector deflecting the particle beam into the irradiation nozzle,
wherein the irradiation nozzle is moved vertically by variation of the length (L) of the telescope section.

33. The irradiation device according to claim 32, wherein the nozzle swivel axis is horizontal and/or the particle beam enters into the telescope arm in horizontal direction and is deflected into the telescope section.

34. The irradiation device according to claim 32, wherein the vertical and the rotary movements of the irradiation nozzle are coordinated by a control device controlling position and direction of the particle beam irradiated from the irradiation nozzle.

35. The irradiation device according to claim 32, wherein at least two of the three movements
(i) horizontal movement of the support
(ii) vertical movement of the irradiation nozzle
(iii) rotary movement of the irradiation nozzle
are coordinated by a control device in such a way that the particle beam keeps impinging onto the irradiation object when the support and/or the irradiation nozzle is moved.

36. The irradiation device according to claim 32,
wherein the horizontal movement of the support and the vertical and rotary movements of the irradiation nozzle are coordinated by a control device in such a way that the particle beam impinges onto the irradiation object at a defined distance from the irradiation nozzle when the support and/or the irradiation nozzle is moved.

37. An irradiation device for irradiating an irradiation object with heavy charged particles, comprising:
a support for the irradiation object; and
an irradiation nozzle irradiating a charged particle beam towards the irradiation object,
wherein the particle beam is deflected within the irradiation nozzle,
wherein the support for the irradiation object is moveable at least horizontally,
wherein the irradiation nozzle is moveable at least vertically and is rotatable around a nozzle swivel axis along which the particle beam enters into the irradiation nozzle, and
wherein the vertical movement of the irradiation nozzle is effected by arranging a particle beam source, a beam guidance device guiding the particle beam into the irradiation nozzle, and the irradiation nozzle on a platform, the platform being at least movable vertically.

38. An irradiation device for irradiating an irradiation object with heavy charged particles, comprising:
a support for the irradiation object; and
an irradiation nozzle irradiating a charged particle beam towards the irradiation object, wherein the particle beam is deflected within the irradiation nozzle, wherein the support for the irradiation object is moveable at least horizontally, and wherein the irradiation nozzle is moveable at least vertically and is rotatable around a nozzle swivel axis along which the particle beam enters into the irradiation nozzle, the irradiation device further comprising, upstream from the irradiation nozzle, a particle beam deflector allowing to deflect the particle beam to variable inclinations compared to a horizontal plane in such a way that the particle beam can enter into the irradiation nozzle at various vertical elevations.

39. The irradiation device according to claim 38, wherein the vertical and the rotary movements of the irradiation nozzle are coordinated by a control device controlling position and direction of the particle beam irradiated from the irradiation nozzle.

40. The irradiation device according to claim 38, wherein at least two of the three movements
   (i) horizontal movement of the support
   (ii) vertical movement of the irradiation nozzle
   (iii) rotary movement of the irradiation nozzle
are coordinated by a control device in such a way that the particle beam keeps impinging onto the irradiation object when the support and/or the irradiation nozzle is moved.

41. The irradiation device according to claim 38,
wherein the horizontal movement of the support and the vertical and rotary movements of the irradiation nozzle are coordinated by a control device in such a way that the particle beam impinges onto the irradiation object at a defined distance from the irradiation nozzle when the support and/or the irradiation nozzle is moved.

42. The irradiation device according to claim 38,
wherein an angle between a direction of the particle beam impinging onto the irradiation object and the vertical direction can be varied between 0° and +180°.

43. The irradiation device according to claim 38, wherein the support for the irradiation object is rotatable around a vertical axis by 180°.

44. A method for irradiating an irradiation object with heavy charged particles from various angular directions, comprising:
   placing the irradiation object onto a support, which is moveable at least horizontally;
   irradiating a charged particle beam from an irradiation nozzle along a certain irradiation direction towards the irradiation object;
   deflecting the particle beam within the irradiation nozzle; and
   changing the irradiation direction by moving the support at least horizontally and by moving the irradiation nozzle at least vertically and rotating the irradiation nozzle around a swivel axis, along which the particle beam enters the irradiation nozzle,
   wherein the particle beam is configured to enter into the irradiation nozzle at various vertical elevations by deflecting, upstream from the irradiation nozzle, the particle beam to variable inclinations compared to a horizontal plane.

45. The method according to claim 44, wherein a distance from the irradiation nozzle to the irradiation object is maintained constant while the irradiation direction is changed by moving and/or rotating the irradiation nozzle and/or moving the support.

46. The method according to claim 44, further comprising coordinating at least two of the three movements
   (i) horizontal movement of the support
   (ii) vertical movement of the irradiation nozzle
   (iii) rotary movement of the irradiation nozzle
in such a way that the particle beam keeps impinging onto the irradiation object when the support and/or the irradiation nozzle is moved.

* * * * *